(12) United States Patent
Cui et al.

(10) Patent No.: US 10,857,260 B2
(45) Date of Patent: Dec. 8, 2020

(54) COAXIAL NEEDLE FOR FABRICATING A MULTI SCALE, MULTI LAYER BLOOD VESSEL OR VASCULAR NETWORK EMPLOYING 3D BIOPRINTING

(71) Applicant: The George Washington University, Washington, DC (US)

(72) Inventors: Haitao Cui, Arlington, VA (US); Wei Zhu, Washington, DC (US); Lijie Grace Zhang, Washington, DC (US)

(73) Assignee: The George Washington University, Washington, DC (US)

( * ) Notice: Subject to any disclaimer, the term of this patent is extended or adjusted under 35 U.S.C. 154(b) by 364 days.

(21) Appl. No.: 15/864,387

(22) Filed: Jan. 8, 2018

(65) Prior Publication Data
US 2019/0008998 A1 Jan. 10, 2019

Related U.S. Application Data

(60) Provisional application No. 62/445,599, filed on Jan. 12, 2017.

(51) Int. Cl.
*A61L 27/38* (2006.01)
*A61L 27/50* (2006.01)
(Continued)

(52) U.S. Cl.
CPC .............. *A61L 27/16* (2013.01); *A61L 27/18* (2013.01); *A61L 27/222* (2013.01); *A61L 27/3808* (2013.01); *A61L 27/3826* (2013.01); *A61L 27/507* (2013.01); *A61L 27/52* (2013.01); *B29C 64/118* (2017.08); *B29C 64/209* (2017.08);
(Continued)

(58) Field of Classification Search
CPC ................... A61F 2/062; A61L 27/222; A61L 27/507–54; A61L 27/3826; A61L 27/3834; A61L 27/3808
See application file for complete search history.

(56) References Cited

U.S. PATENT DOCUMENTS 9,315,043 B2 4/2016 Murphy et al.
2016/0288414 A1* 10/2016 Ozbolat ............... B29C 64/393
(Continued)

FOREIGN PATENT DOCUMENTS

WO WO 2015/048355 A1 4/2015

OTHER PUBLICATIONS

Yang et al., "Mussel-Inspired Human Gelatin Nanocoating for Creating Biologically Adhesive Surfaces," International Journal of Nanomedicine, 2014, vol. 9, pp. 2753-2765.
(Continued)

*Primary Examiner* — Thaddeus B Cox
(74) *Attorney, Agent, or Firm* — Kory D. Christensen

(57) ABSTRACT

A coaxial needle having two or more passageways for forming a biomimetic bioprinted blood vessel tubular construct. The coaxial needle has an external needle passageway and an internal needle passageway separated by an internal barrier, and having a nozzle at an end thereof. A bioink is provided flowable through the external needle passageway and a crosslinking solution is provided flowable through the internal needle passageway. The crosslinking solution contacts the bioink as the crosslinking solution and bioink exit the nozzle thereby forming a tubular blood vessel construct.

23 Claims, 16 Drawing Sheets

(51) Int. Cl.
| | |
|---|---|
| A61L 27/52 | (2006.01) |
| A61F 2/06 | (2013.01) |
| A61L 27/16 | (2006.01) |
| A61L 27/18 | (2006.01) |
| B29C 64/209 | (2017.01) |
| B33Y 10/00 | (2015.01) |
| B33Y 30/00 | (2015.01) |
| B29C 64/118 | (2017.01) |
| A61L 27/22 | (2006.01) |
| B29C 64/135 | (2017.01) |
| B33Y 70/00 | (2020.01) |

(52) U.S. Cl.
CPC .............. B33Y 10/00 (2014.12); B33Y 30/00 (2014.12); *A61F 2/062* (2013.01); *A61L 2430/22* (2013.01); *B29C 64/135* (2017.08); *B33Y 70/00* (2014.12)

(56) References Cited

U.S. PATENT DOCUMENTS

2018/0110901 A1* 4/2018 Lewis .................... A61L 27/56
2018/0117171 A1* 5/2018 Mooney ................. A61K 39/00
2018/0280578 A1* 10/2018 Hwang ................... B29C 67/02

OTHER PUBLICATIONS

Van De Walle, et al., "Polydopamine-Gelatin as Universal Cell-Interactive Coating for Methacrylate-Based Medical Device Packaging Materials: When Surface Chemistry Overrules Substrate Bulk Properties," American Cancer Society, Biomacromolecules, 2016, vol. 17, pp. 56-58.
Nichol et al., "Cell-Laden Microengineered Gelatin Methacrylate Hydrogels," National Institutes of Health, Biomaterials, Jul. 2010, 31(21), pp. 1-20.
Bersini et al., "3D Functional and Perfusable Microvascular Networks for Organotypic Microfluidic Models," J. Mater. Sci. Mater. Med. 26, 180 pp. 1-11 (2015).
Briquez et al., "Design Principles for the Therapeutic Angiogenic Materials," Nature Review, Materials, vol. 1, Jan. 2016, pp. 1-15.
Brodde, "Vascular Dopamine Receptors: Demonstration and Characterization by In Vitro Studies," Life Life Sciences, vol. 31, No. 4, 1982, pp. 289-306.
Chistiakov et al., "Effects of Shear Stress on Endothelial Cells: Go with the Flow," Acta Physiol. 219, 382-408 (2017).
Chiu et al., "Effects of Disturbed Flow on Vascular Endothelium: Pathophysiological Basis and Clinical Perspectives," Physiol. Rev. 91, pp. 1-106 (2011).
Chlupac et al., "Blood Vessel Replacement: 50 Years of Development and Tissue Engineering Paradigms in Vascular Surgery," Physiol. Res. 58 (Suppl. 2): pp. S119-S139, 2009.
Cui et al., "3d Bioprinting for Organ Regeneration," Adv. Healthcare Mater. 6, (2017), pp. 1-54.
Cui et al., "Biologically Inspired Smart Release System Based on 3D Biprinted Perfused Scaffold for Vascularized Tissue Regeneration," Adv. Sci. 2016, vol. 3, pp. 1-10.
Cui et al., Hierarchical Fabrication of Engineered Vascularized Bone Biphasic Constructs Via Dual 3D Bioprinting: Integrating Regional Bioactive into Architectural Design, Adv Healthc Mater. Sep. 2016; 5(17), pp. 1-13.
Elliott et al., "Three-dimensional Culture of Small-Diameter Vascular Grafts," J. Mater Chem. B 4, 3443-3453 (2016).
Forfacs, "Perfusable Vascular Networks," Nature Materials, vol. 11, Sep. 2012, pp. 746-747.
Gui, PhD., et al., "Vascular Tissue Engineering: Building Perfusable Vasculature for Implantation," Curr. Opin. Chem. Eng. 3, pp. 1-14 (2014).
Haga et al., "Molecular Basis of the Effects of Mechanical Stretch on Vascular Smooth Muscle Cells," J. Biomech. 40, 947-960 (2007).
Hasan et al., "Microfluidic Techniques for Development of 3D Vascularized Tissue," Biomaterials 35, pp. 1-38 (2014).
Hoch et al., "Bioprinting of Artificial Blood Vessels: Current Approaches Towards a Demanding Goal," European Journal of Cardio-Thoracic Surgery vol. 46 (2014) pp. 767-778.
Hong et al., "Hyaluronic Acid Catechol: a Biopolymer Exhibiting a pH-Dependent Adhesive or Cohesive Property for Human Neural Stem Cell Engineering," Adv. Funct. Mater. 2013, vol. 23, pp. 1774-1780.
Huang et al., "Engineering of Arteries in Vitro," Cell Mol Life Sci., Jun. 2014; 71(11): 2013-2018, pp. 1-26.
Koike et al., "Creation of long-lasting blood vessels," Nature 428, (2004) pp. 138-139.
Kolesky et al., "3D Bioprinting of Vascularized, Heterogeneous Cell-Laden Tissue Constructs," Adv. Mater. 2014, vol. 26, pp. 3124-3130.
Kolesky et al., "Three-Dimensional Bioprinting of Thick Vaslcularized Tissues," PNAS, Mar. 22, 2016, vol. 13, No. 12, pp. 3179-3184.
Koshy et al., "Injectable, Porpous, and Cell-Responsive Gelation Cryogels," Biomaterials Mar. 2014; 35(8), pp. 1-20.
Lee et al., "Alginate: Properties and Biomedical Applications," Prog Polym Sci, Jan. 2012; 37(1): 106-126, pp. 1-45.
Lee et al., "Synthesis and Gelation of DOPA-Modified Poly (ethylene glycol) Hydrogels," Bimacromolecules, 2002, 3, pp. 1038-1047.
Lehoux et al., "Cellular Mechanics and Gene Expression in Blood Vessels, " J. Biomech. 36, 631-643 (2003).
Lesman et al., "Mechanical Regulation of Vascular Network Formation in Engineered Matrices," Advanced Drug Delivery Reviews vol. 26, 2016, pp. 176-182.
Li et al., "Molecular Basis of the Effects of Shear Stress on Vascular Endothelial Cells," J. Biomech. 38, 1949-1971 (2005).
Li et al., "Novel Mussel-Inspired Injectable Self-Healing Hydrogel with Anti-Biofouling Property," Adv. Mater. 2015, vol. 27, pp. 1294-1299.
Liu et al., "Polydopamine and Its Derivative Materials: Synthesis and Promising Applications in Energy, Environmental, and Biomedical Fields," Chem. Rev. 2014, 114, pp. 5057-5115.
Loessner et al., "Functionalization, Preparation and Use of Cell-Laden Gelatin Methacryloyl-Based Hydrogels as Modular Tissue Culture Platforms," Nature Protocols, vol. 11, No. 4, 2016, pp. 727-746.
Miller et al., "Rapid Casting of Patterned Vascular Networks for Perfusable Engineered 3D Tissues," Nat Mater, Sep. 2012, 11(9), pp. 1-16.
Nemeno-Guanzon et al., "Trends in Tissue Engineering for Blood Vessels," J. Biomed. Biotechnol. 2012, 956345 (2012) pp. 1-14.
Novosel et al., Adv. "Vascularization is the Key Challenge in Tissue Engineering," Drug Deliv. Rev. 63, 300-311 (2011).
Ozbolat et al., "Current Advances and Future Perspectives in Extrusion-Based Bioprinting," Biomaterials 76, 321-343 (2016).
Park et al., "Catechol-Functionalized Hyaluronic Acid Hydrogels Enhance Angiogenesis and Osteogenesis of Human Adipose-Derived Stem Cells in Critical Tissue Defects," Biomacromolecules 2016, 17, pp. 1939-1948.
Paulsen et al., "Tissue Vascularization Through 3D Printing: Will Technology Bring Us Flow," Developmental Dynamics, vol. 244, 2015, pp. 629-640.
Potente et al., "Basic and Therapeutic Aspects of Angiogenesis," Cell 146, 873-887 (2011).
Rouwkema et al., "Vascularization and Angiogenesis in Tissue Engineering: Beyond Creating Static Networks," Trends Biotechnol. 34, 733-745 (2016).
Seifu et al., "Small-Diameter Vascular Tissue Engineering," Nat. Rev. Cardiol. 10, 410-421 (2013).
Shin et al., "Complete Prevention of Blood Loss with Self-Sealing Haemostatic Needles," Nature Materials, vol. 16, Jan. 2017, pp. 1-8.
Shin et al., Tissue Adhesive Catechol-Modified Hyaluronic Acid Hydrogel for Effective, Minimally Invasive Cell Therapy, Adv. Funct. Mater. 2015, 25, pp. 3814-3824.

(56) References Cited

OTHER PUBLICATIONS

Thottappillil et al., "Scaffolds in Vascular Regeneration: Current Status," Vasc. Health Risk Manag. 11, 79-91 (2015).
Woodruff, "Dopamine Receptors: a Review," Comp. Gen. Pharmac., 1971, 2, pp. 439-455.
Zhang et al., "Biodegradable Scaffold with Built-in Vasculature for Organ-on-a-chip Engineering and Direct Surgical Anastomosis," Nat Mater. Jun. 2016; 15(6) pp. 1-28.

* cited by examiner

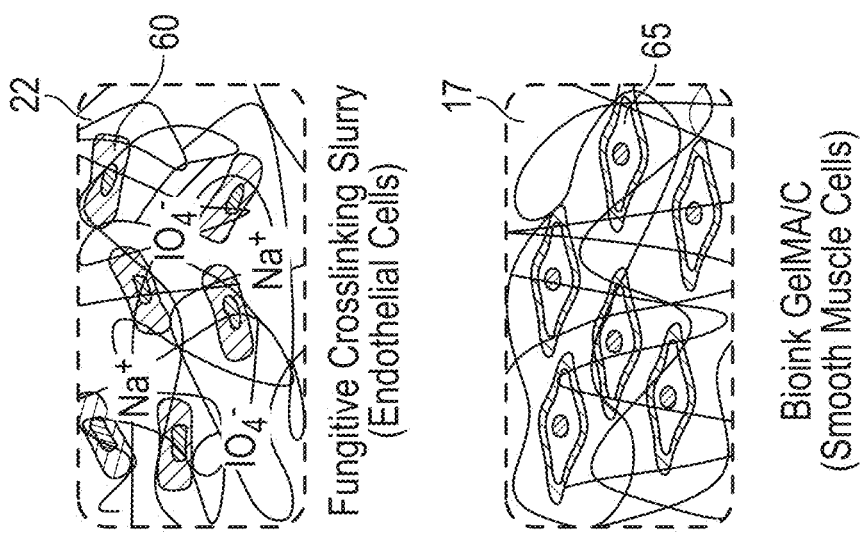
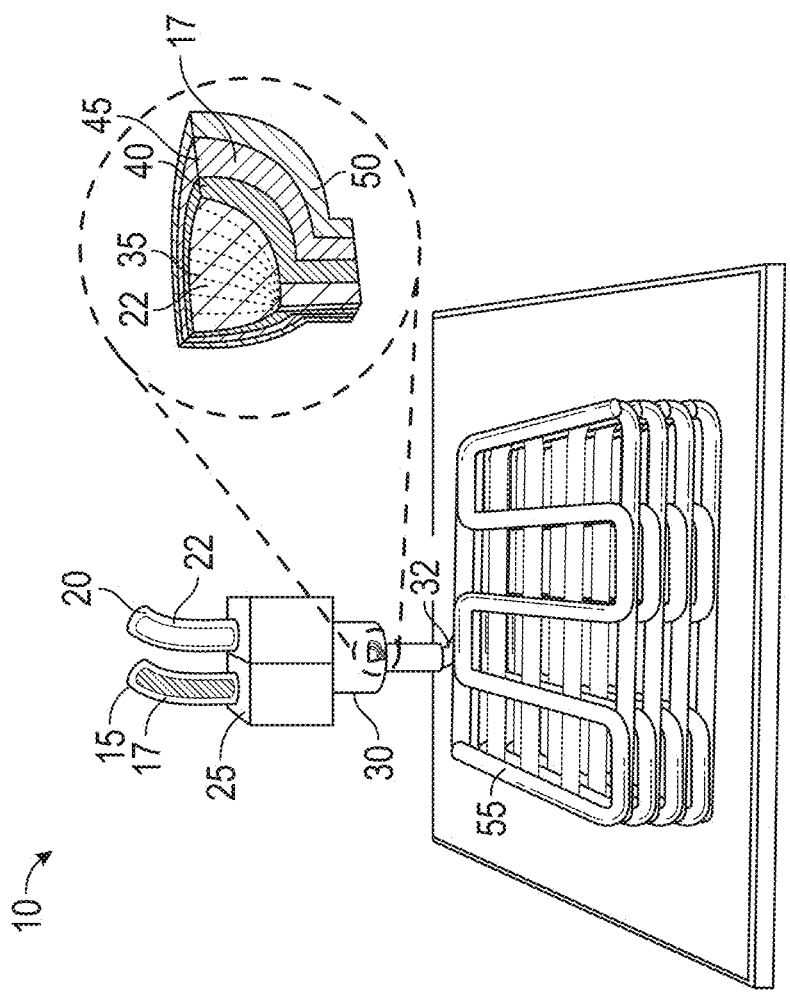
FIG. 4A

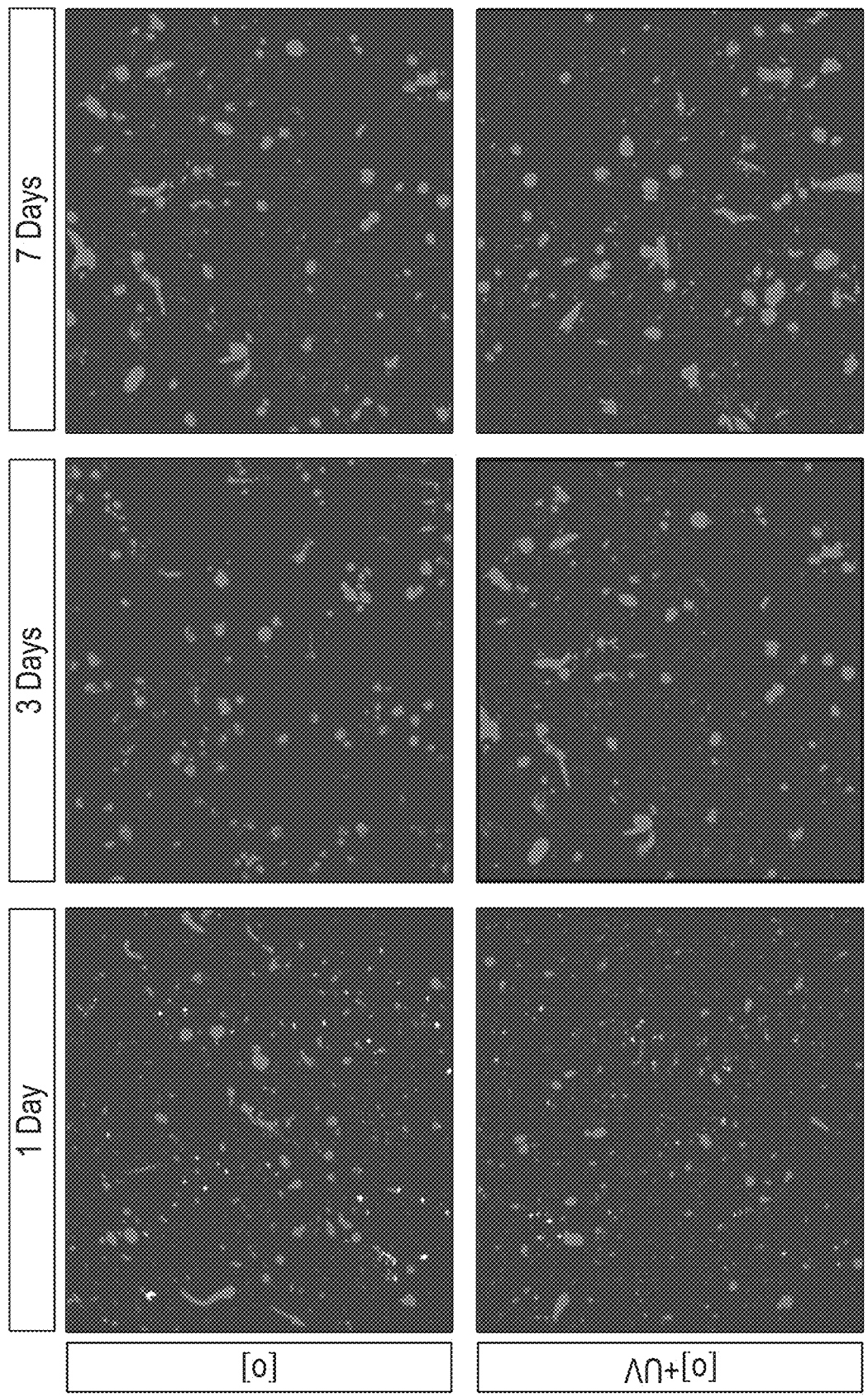

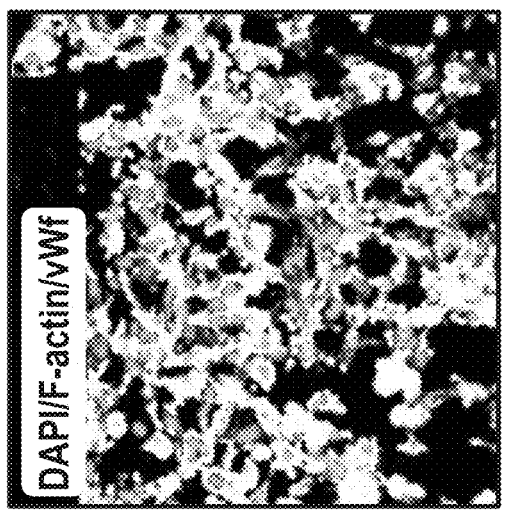
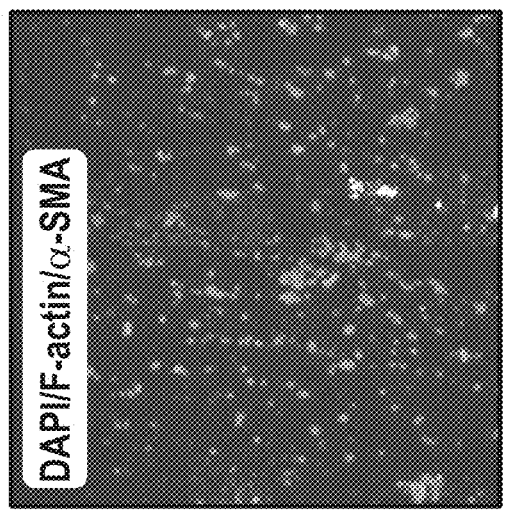
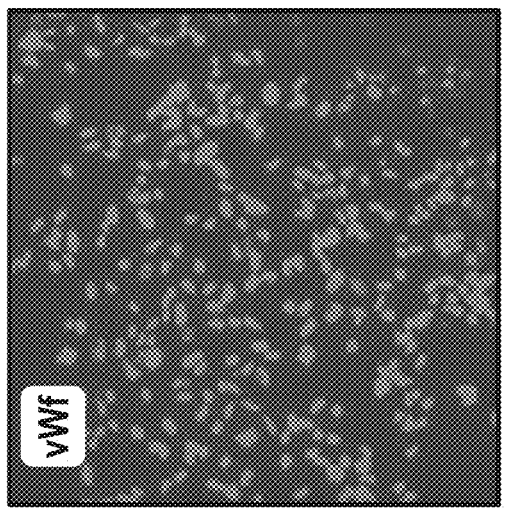
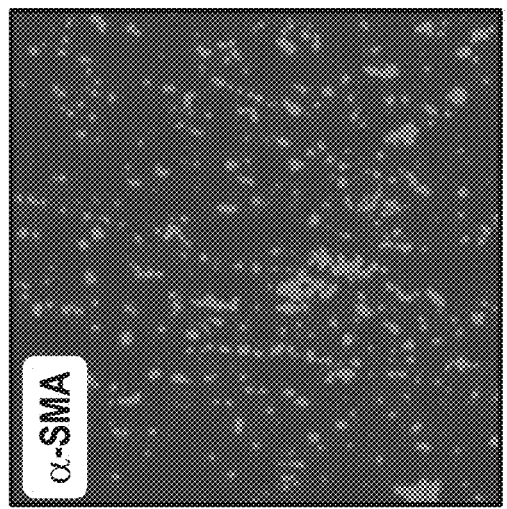
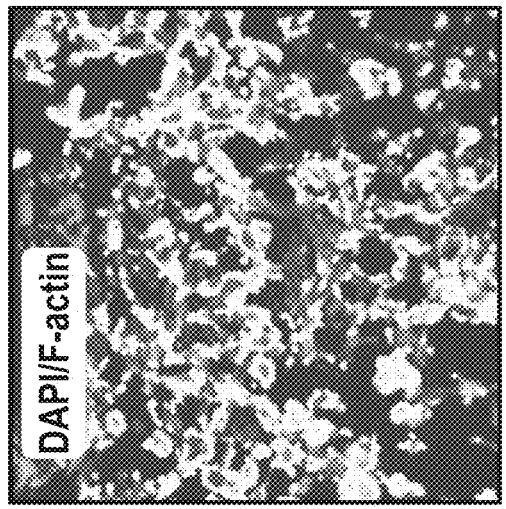
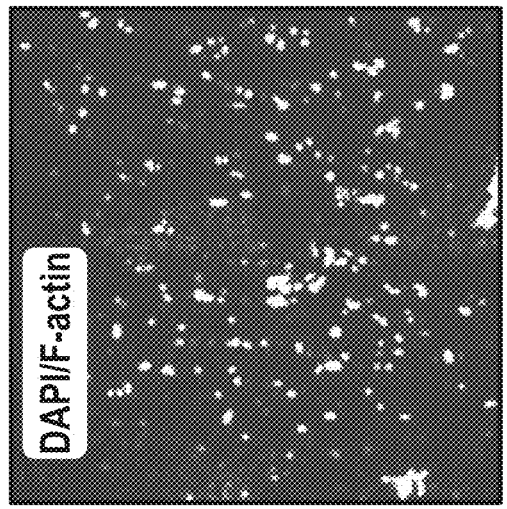
FIG. 12A  FIG. 12B  FIG. 12C

COAXIAL NEEDLE FOR FABRICATING A MULTI SCALE, MULTI LAYER BLOOD VESSEL OR VASCULAR NETWORK EMPLOYING 3D BIOPRINTING

CROSS-REFERENCE TO RELATED APPLICATIONS

The present application claims the benefit of U.S. Provisional Application No. 62/445,599, filed Jan. 12, 2017, which is hereby incorporated by reference in its entirety.

U.S. GOVERNMENT SUPPORT

This invention was made with government support under Grant No. DP2 OD019144 awarded by the NIH. The government has certain rights in the invention.

TECHNICAL FIELD

The present disclosure relates to fabricating artificial blood vessels or vascular network using biomanufacturing technology, and in particular using 3D bioprinting and tailored bioinks to form biomimetic blood vessel constructs.

BACKGROUND

The ability to fabricate artificial tissues/organs that recapitulate the multi-scale structural, mechanical, physiochemical and essential aspects of biological functions is highly critical for future clinical tissue and organ implantation applications. One significant challenge facing the development of large-scale artificial tissue for defect reconstruction is vascularization of complex tissue implants.

3D bioprinting techniques can precisely control the location of biomaterials and cells, making it an effective, comprehensive method for fabricating complicated macro and micro structures that may address the urgent needs of complex tissue manufacturing. Current 3D bioprinting methods for creating vasculature mainly utilize sacrificial templates to fabricate vascular lumen. However, all cases fail to generate multi-scale, multilayer and independent blood vessels that replicate the geometry, complexity, and longevity of human vascularized tissues.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIG. 4A is a diagram of an exemplary coaxial needle;

FIGS. 9A, 9B, 9C are images of live-dead cell staining of smooth muscle cells encapsulated in a blood vessel hydrogel after 1, 3 and 7 day cultures, respectively;

FIGS. 12A, 12B, and 12C illustrate locally amplified immunofluorescence staining of the 3D bioprinted blood vessels cultured in a bioreactor for 2 weeks.

DETAILED DESCRIPTION

Figure 1A:
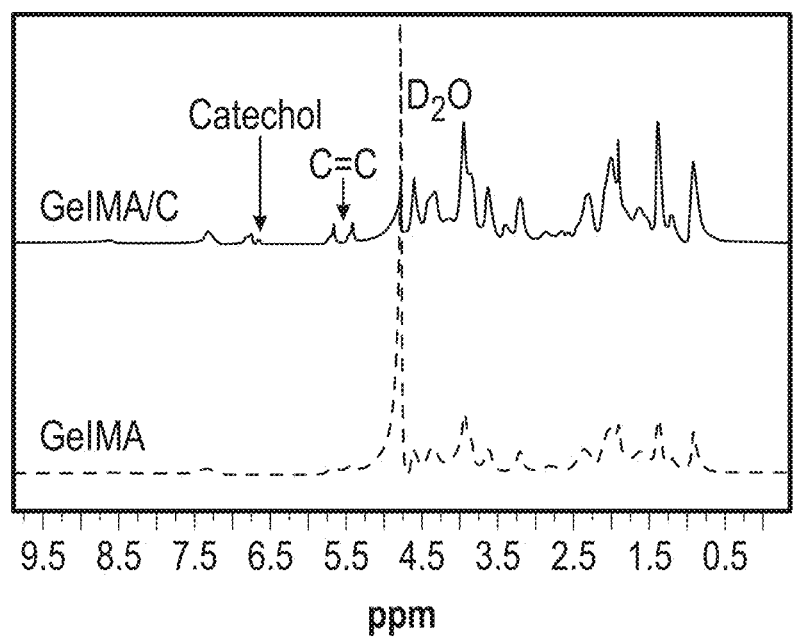
FIG. 1A is an exemplary graph illustrating a $^1$H NMR spectra of gelatin methacrylate/catechol (GelMA/C)

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. It should be understood at the outset that although illustrative implementations of one or more embodiments are illustrated below, the disclosed compositions and methods may be implemented using any number of techniques. The disclosure should in no way be limited to the illustrative implementations, drawings, and techniques illustrated herein, but may be modified within the scope of the appended claims along with their full scope of equivalents.

As used herein, the term "derivative" refers to any compound that is made from a parent compound, for example, by replacing one atom in one of the listed compounds with another atom or group of atoms, adding substituents, ionizing one of the listed compounds, or creating a salt of one of the listed compounds.

Provided herein is a new biomanufacturing method for directly creating blood vessels with multilayer cells and independent architecture. This may be carried out, as disclosed herein, via an in situ artificial blood vessel biomanufacturing technology combining 3D bioprinting and tailored bioinks. The cell-laden bioinks can facilitate the printing of a self-supporting tubular structure and subsequent fabricating of the external tissue architectures with little to no patterned distortion. This method can directly create blood vessels or vascular network with multilayer cells and independent architecture. The artificial blood vessel may be independently printed in any engineered tissue implant, which can transport oxygen and nutrients for the integrated matrix through perfused microcirculation.

The present disclosure relates to combining a novel bioactive ink and 3D bioprinting method to directly create blood vessels or vascular networks with multilayer cells and independent architecture. Disclosed herein is an extrusion printer with a coaxial nozzle and a new printable cell-laden bioink (gelatin methacrylate/catechol (GelMA/C)) to directly fabricate the bilayer blood vessel. As disclosed herein, bioprinting may be performed using a coaxial needle extrusion system, having an external needle passageway and an internal needle passageway. A bioink mixture containing GelMA/C and smooth muscle cells (SMCs) may be flowed through the external needle passageway. Additionally, a crosslinking solution having Pluronic® F127 bioreagent/NaIO3 along with endothelial cells (ECs) may be flowed through the internal needle passageway. When the crosslinking solution comes in contact with the bioink, the catechol groups of GelMA/C are rapidly crosslinked to form a self-supporting, biomimetic blood vessel with a bilayer cell structure (SMCs encircle ECs). The methacrylate groups further contribute to modulation of the elastic moduli and immobilization of with bioactive factors under ultra violet (UV) laser exposure. The presently disclosed 3D bioprinted vasculature technique and apparatus also promotes myogenesis and angiogenesis.

Various printing parameters may be adjusted, such as nozzle diameter, printing speed, flow velocity of bioink, and others, which may change the wall thickness and diameter of blood vessels for the multi-scale fabrication. In addition, the coaxial needle may be multi-coaxial, having a plurality of needle passageways each forming a layer, such as three or more, where each layer may be extruded with different cells for the fabrication of multilayer blood vessel constructs. Such multi-coaxial needle may have an external needle passageway and an internal needle passageway and one or more passageways layered between the external and internal needle passageways.

Bioink

The bioink as disclosed herein may be rapidly solidified to elastomeric and self-standing hydrogel. The bioink may be formed by reacting a gelatin to form gelatin methacrylate which is then further functionalized with a crosslinkable group such as a catechol. In order to synthesize the catechol modified gelatin methacrylate, an exemplary two step chemical reaction may be employed where gelatin is successively reacted with methacrylic anhydride and then dopamine as follows:

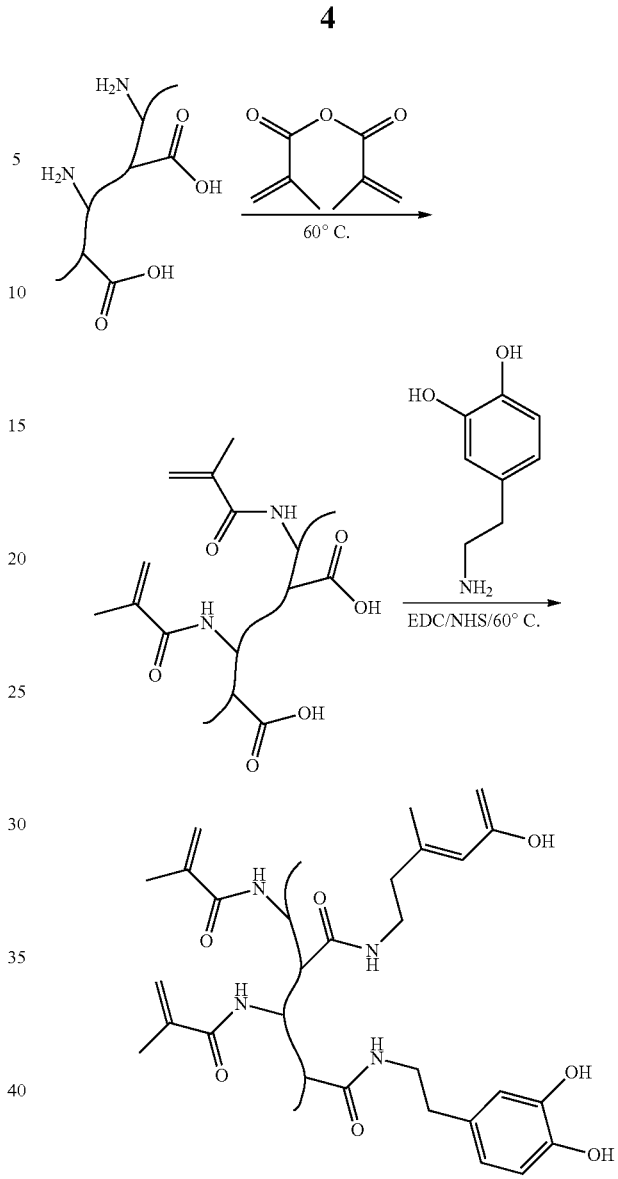

As illustrated, a gelatin may first be modified with methacrylic anhydride to form gelatin methacrylate (referred to herein as "GelMA"). Thereafter the GelMA maybe modified to include a crosslinkable group such as a catechol by reacting the GelMA with dopamine in a solvent containing 1-ethyl-3-(3-(dimethylamino)-propyl) carbodiimide (EDC) and N-hydroxysulfosuccinimide (NHS), the resulting compound referred to herein as GelMA/C. Mole ratios of (—NH$_2$)/GelMA (—COOH) may range from 10:1 and 5:1. Alternative to dopamine, other catecholamines may be suitably employed to functionalize the GelMA with a catechol or amine substituted benzenediols, benezepolyols or phenols. Illustrated in FIG. 1A is a $^1$H NMR spectra of gelatin methacrylate/catechol (GelMA/C), illustrating the successful conjugation of dopamine onto GelMA.

The GelMA/CA may be crosslinked by an oxidant such as a periodate salt, or derivatives thereof, such as sodium periodate, NaIO$_4$, which causes gelation of the GelMA/CA, the crosslinking illustrated as follows:

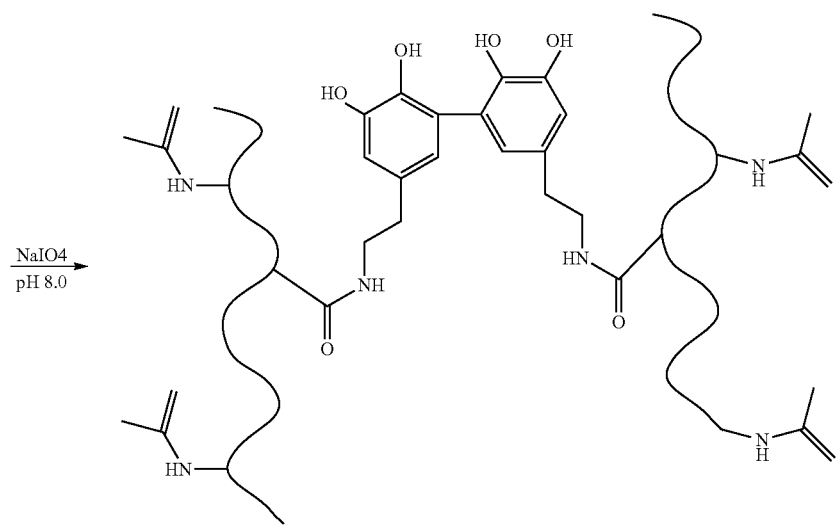

Oxidation Crosslinking

Figure 1B:
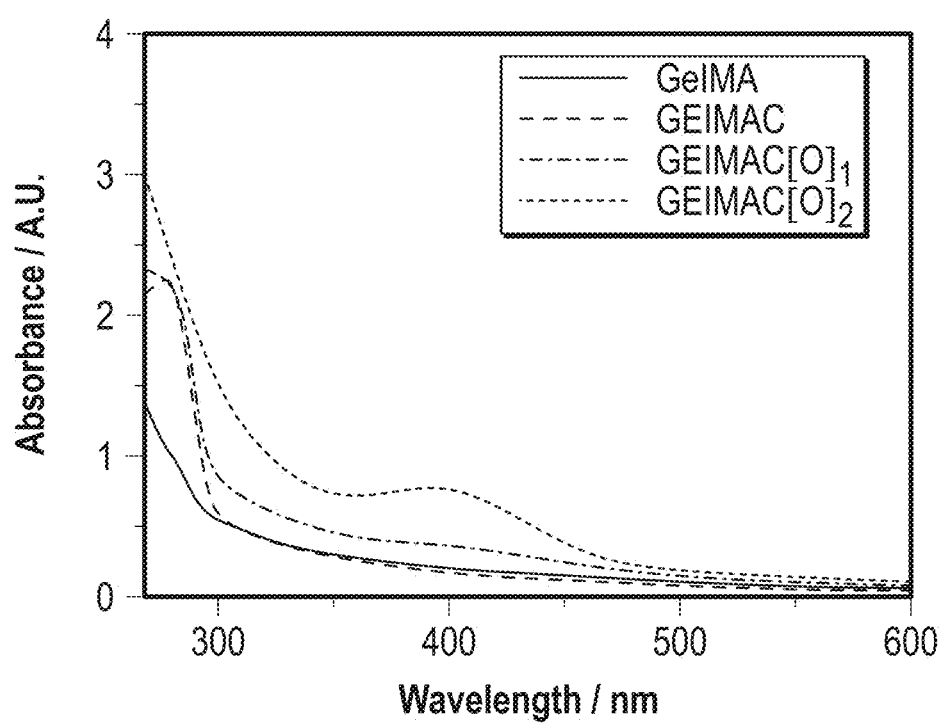
FIG. 1B is an exemplary graph illustrating UV-Vis spectra of GelMA/C and its oxidization product solutions.
Figure 1C:
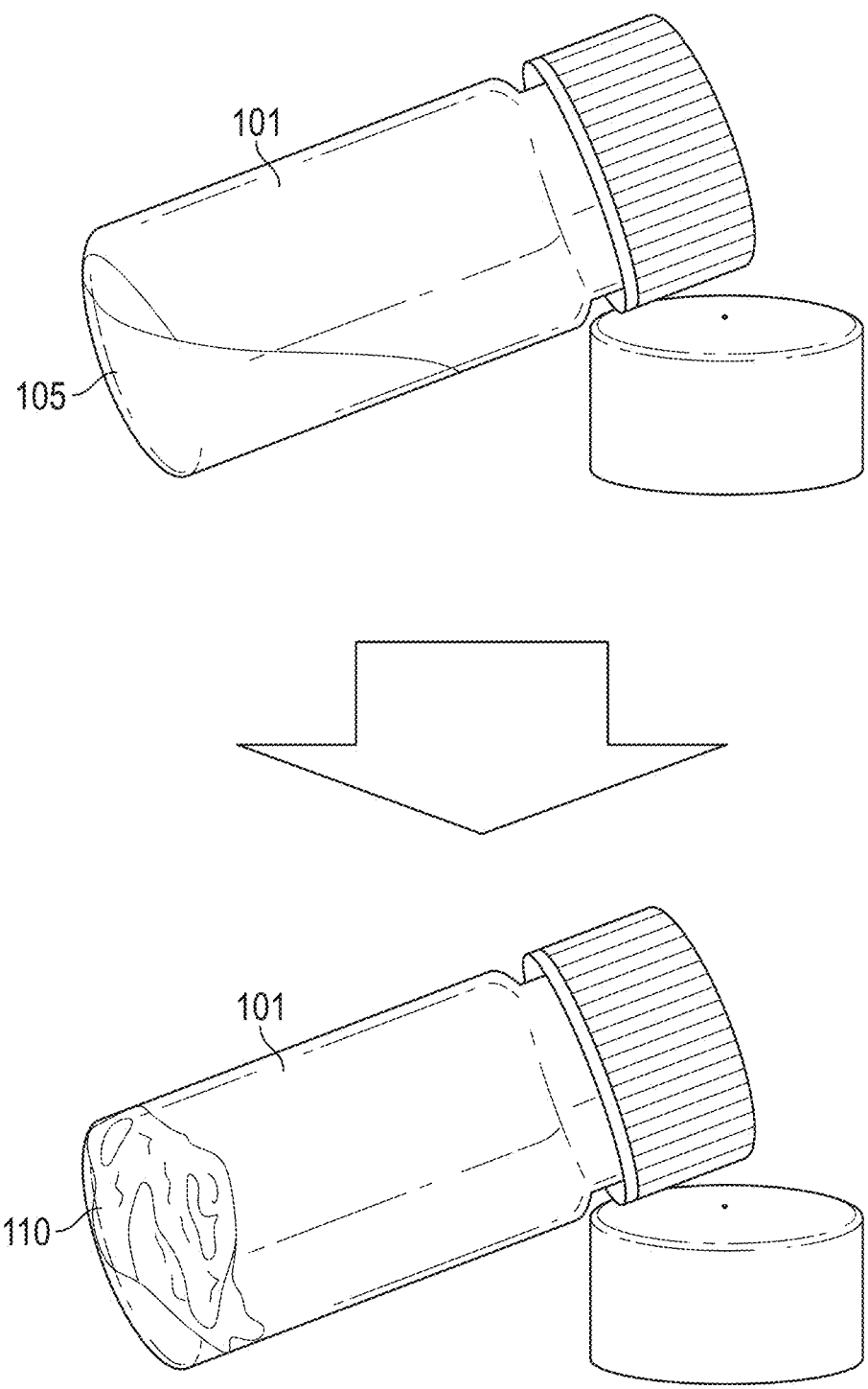
FIG. 1C is a diagram illustrating a container having GelMA/C.

FIG. 1B shows UV-Vis spectra of GelMA/C and its oxidization product solutions (treated with sodium periodate, NaIO4). As a result of the crosslinking, a self supporting structure is formed, for example as shown in FIG. 1C wherein the liquid GelMA/C 105 in container 101 is formed into a self supporting hydrogel structure 110 in container 101.

Figure 2A:
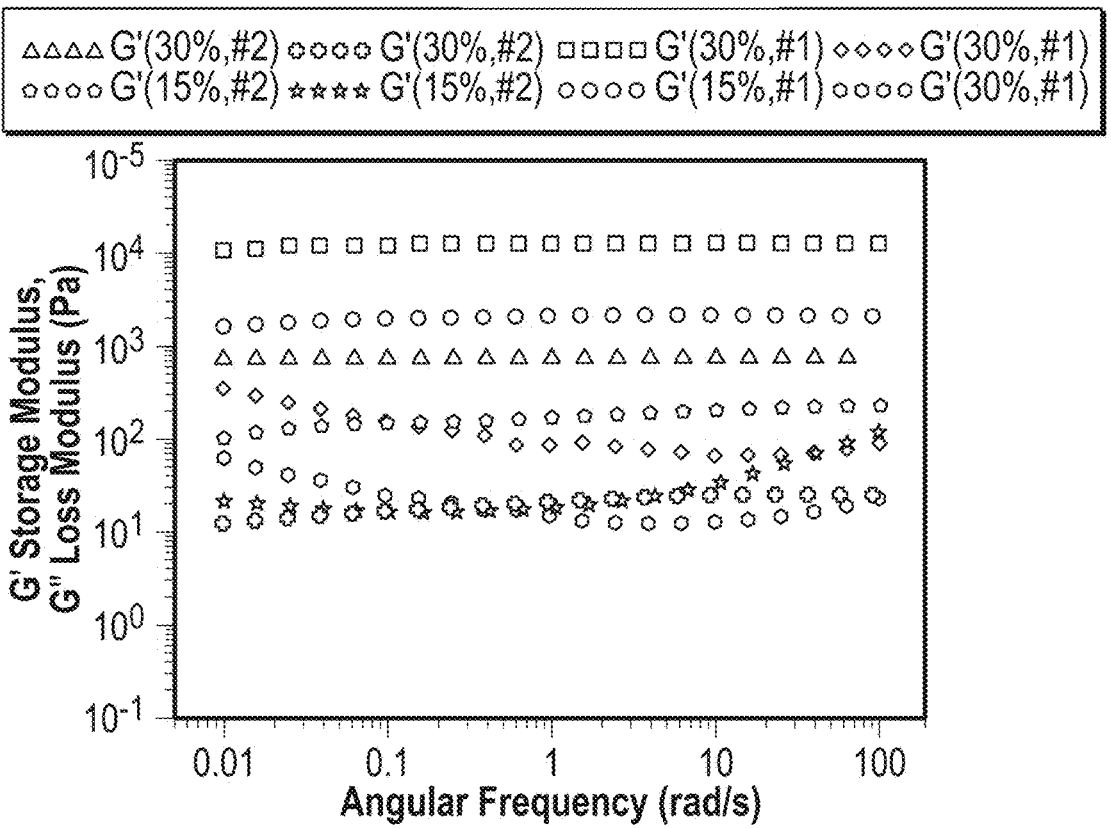
FIG. 2A is an exemplary graph showing rheological properties of a hydrogel with respect to angular frequency.
Figure 2B:
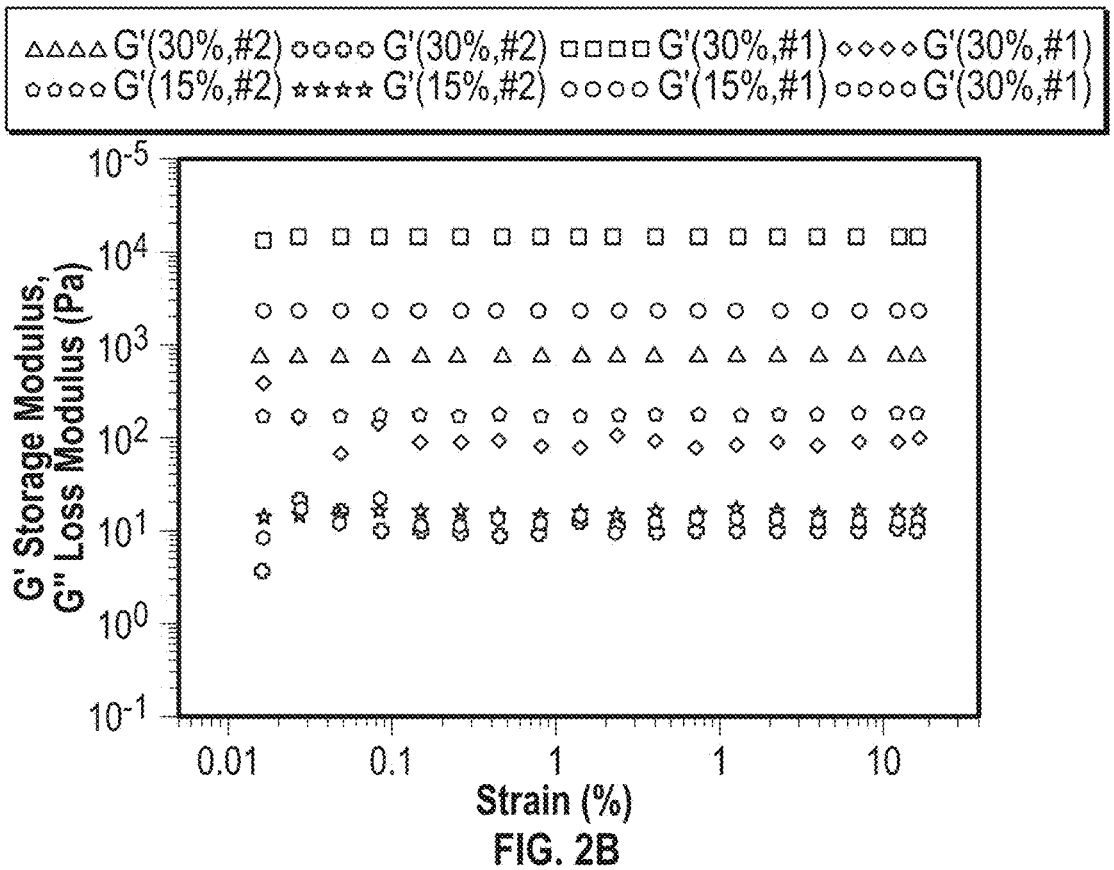
FIG. 2B is an exemplary graph showing rheologial properties of a hydrogel with respect to strain.

Furthermore, rheologial properties of the hydrogel are illustrated including angular frequency in FIG. 2A, and strain in FIG. 2B tested using a rheometer. Storage modulus and loss modulus changes with varying concentration, with #1: 3.2 w/w % and #2: 1.4 w/w %.

Figure 3:
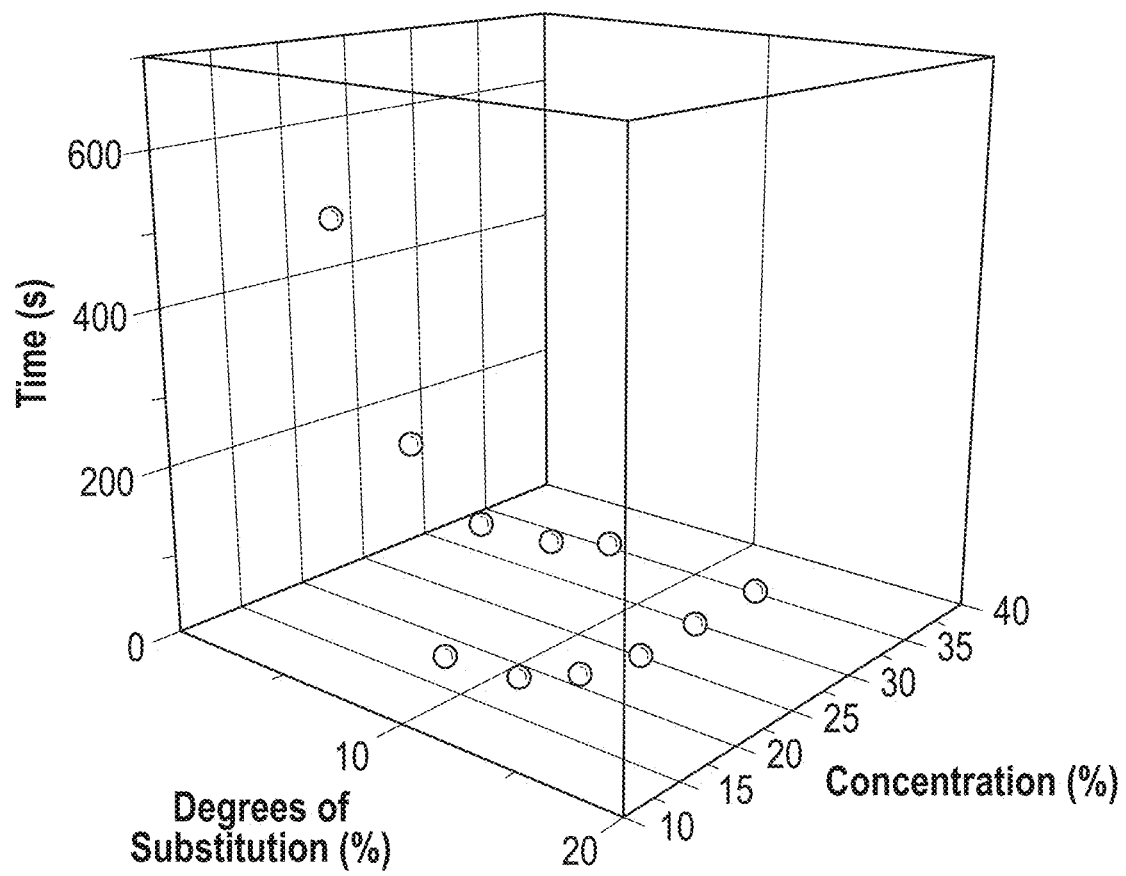
FIG. 3 is a graph illustrating the gelation time of GelMA/C solutions when varying DS of catechol and solution concentration.

Furthermore, as shown in FIG. 3, the gelation time of GelMA/C depends on the degree of substitution of catechol, and solution concentration. Degrees of substitution may range from 5% to 40%, alternatively from 10% to 35%, alternatively from 15% to less than 30%, encompassing any value and subset therebetween.

The bioink may further contain various cells which may be incorporated to form a component of the outer layer of the tubular blood vessel construct. Such cells may be smooth muscle cells, and may provide strength to the tubular structure to act as a blood vessel. Exemplary smooth muscle cells may be human or animal, and for instance may include vascular smooth muscle cells including coronary artery smooth muscle cells, aortic smooth muscle cells, umbilical artery smooth muscle cells and pulmonary smooth muscle cells.

Crosslinking Solution

The crosslinking solution disclosed herein may include a crosslinking agent such as an oxidant. When the oxidant in the crosslinking solution contacts the bioink, the catechol groups of the GelMA/C are crosslinked. The catechol groups may be crosslinked to form filaments with a core-shell structure. Exemplary oxidants suitable for use according to the present disclosure includes tyrosinase, peroxides such as hydrogen peroxide ($H_2O_2$), sodium periodate ($NaIO_4$), and $O_2$. $NaIO_4$ may have relatively more rapid gelation and high biocompatibility both in vitro and in vivo.

The crosslinking solution may also include a fugitive ink. The fugitive ink may be a thermosensitive hydrogel which may serve as structural support for forming the tubular blood vessel during synthesis. After the crosslinking solution reacts with the bioink, the fugitive may be removed by washing with water and/or lowering the temperature (below 10° C.). The fugitive ink may be biologically inert to multiple cell types for short periods of time to allow for the synthesis process of the blood vessel. Exemplary fugitive inks may include a copolymer of hydrophobic polypropylene oxide (PPO) and hydrophilic polyetheylene oxide (PEO), and may be a PEO-PPO-PEO triblock copolymer. An exemplary commercially available fugitive ink includes Pluronic® F127 bioreagent. The fugitive ink is a gel at room temperatures but may transform to solution at low temperature or be dissolved in water.

The crosslinking solution may also include a second set of cells the same or different than the cells in the bioink. The crosslinking solution may include endothelial cells, which may serve as the interior surface of the blood vessel after formation. The cells disclosed herein may be human or animal cells, and may include endothelial cells may include vascular endothelial cells, human umbilical vein endothelial cells (HUVECS), human aortic endothelial cells (HAECs) as well as other suitable cells may be employed herein.

Coaxial Needle

Disclosed herein for forming the biomimetic blood vessels is a coaxial printing system. Illustrated in FIG. 4A is one embodiment of a coaxial needle 10. The coaxial needle 10 may include a bioink input line 15 having a bioink 17 as well as a crosslinking solution input line 20 having a crosslinking solution 22. The bioink input line 15 and crosslinking input line 20 are fluidically coupled with the body 25 of the coaxial needle 10. While a bioink 17 and a crosslinking solution 22 is shown herein input into the coaxial needle 10, there may be other fluids comprising various cells, inks or components as desired for producing the resulting blood vessel constructs.

The bioink 17 as well as crosslinking solution 22 are flowed through the coaxial needle 10 to the coaxial nozzle 30. The coaxial nozzle 30 has an inner passageway 35 as well as an external passageway 45 separated by an internal barrier 40. The internal passageway 35 may be a central bore running along the length of the coaxial needle 10 to the coaxial nozzle 30. The external passageway 45 may be extend between the internal barrier 40 and the external housing 50. The external passageway 45 may be annular, encircling the internal passageway 35. The external passageway may fully or partially encircle a portion of the internal passageway 35. By encircling the internal passageway 35, the tubular shaped construct may be advantageously fully formed. One or more or a plurality of intermediate passageways may be provided between the external passageway 45 and the internal passageway 35 for flowing additional layers for bioprinting containing the same or different cells as the bioink 17 and the crosslinking solution 22.

The external passageway may be a 20 gauge (G) needle size (outer diameter of about 910 μm). The external passage way have any suitable gage and diameter size, but greater than the internal passageway gage and diameter. The external passageway gage may depend on the circumstances and may range from about 15G to 25G (outer diameter of about 1829 μm to about 514 μm). The internal passageway may be 26G (outer diameter of about 500 μm), and may range from 20G to 30G (about 910 μm to 311 μm). The external passageway may range from 0.5 to 10 times, alternatively 2 to 5 times greater than the internal passageway. The size of intermediate passageways (needles) between the external passageway and internal passageway may be sized between the external and internal passageways.

The internal passageway 35 may have a crosslinking solution 22 which may have endothelial cells 60, and the external passageway 45 may have the bioink 17 with smooth muscle cells 65.

As the bioink 17 and the crosslinking solution 22 exit 32 the nozzle 30, the crosslinking solution 22 contacts the bioink 17. As discussed above, the crosslinking solution, having a crosslinking agent such as an oxidant, may crosslink the catechol groups of the GelMA/C in the bioink. As a result, when the crosslinking solution comes into contact with the bioink, the catechol groups of GelMA/C rapidly crosslink to form a self-supporting blood vessel with a bilayered cell structure. The fugitive ink in the crosslinking solution 22 forms a temporary support for the bilayer of cells to form around in the shape of a tubular structure. The fugitive ink template also assists in the crosslinking of the bioink. Additionally, the fugitive ink template anchors endothelial cells in the channel for endothelium formation, and protects them from the harmful effect of the oxidative crosslinker. A blood vessel network 55 may be formed.

Figure 4B:
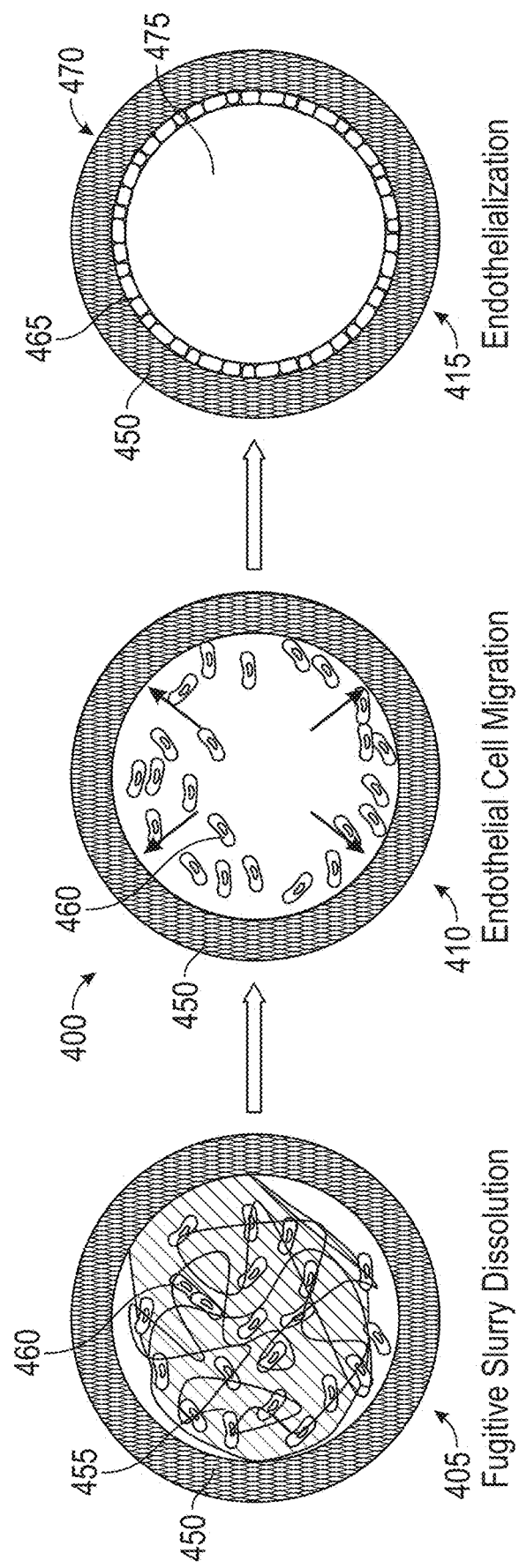
FIG. 4B is a is a diagrammatic flow diagram of endothelial migration and formation of an inner layer of human umbilical vein endothelial cells (HUVEC) cells.

FIG. 4B illustrates a flow diagram 400 of endothelial migration and formation of an inner layer of HUVEC cells. As shown in step 405, a tubular blood vessel structure is provided with the outer shell layer 450 being a crosslinked layer with smooth muscle cells. The core 455 contains the fugitive ink with endothelial cells 460. The fugitive ink dissolves at low temperature or after being washed with water. As shown in step 410 the endothelial cells 460 migrate to the outer core to form an inner layer. As shown in step 415, the bilayer 470 is formed from the inner layer 465 of the migrated endothelial cells and the outer core 455 containing smooth muscle cells. In this way a blood vessel is formed with an inner layer of endothelial cells and an outer layer having smooth muscle cells.

Figure 4C:
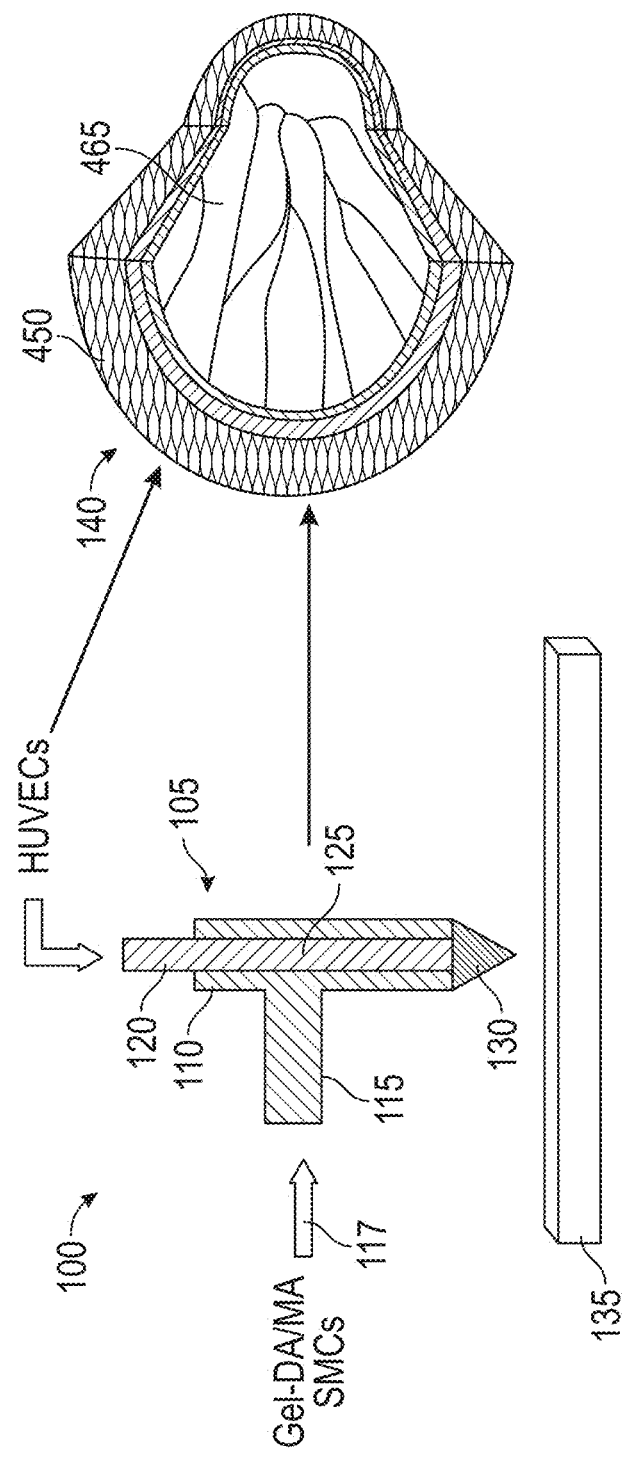
FIG. 4C is a diagram of an exemplary coaxial needle system.

Illustrated in FIG. 4C is an exemplary coaxial needle system 100. The needle 105 has an outer body 110 having the external passageway with a bioink input 115 for bioink 117 having GelMA/C and smooth muscle cells. The crosslinking solution 120 is flowed through the internal passageway 125. The bioink 117 and crosslinking solution 120 is flowed through nozzle 130 to plate 135. Further, as the crosslinking solution 120 contacts the bioink after they exit out of nozzle 130 a tubular blood vessel construct 140 is formed having a shell layer 450 containing smooth muscle cells and an inner layer 465 having endothelial cells.

Figure 5:
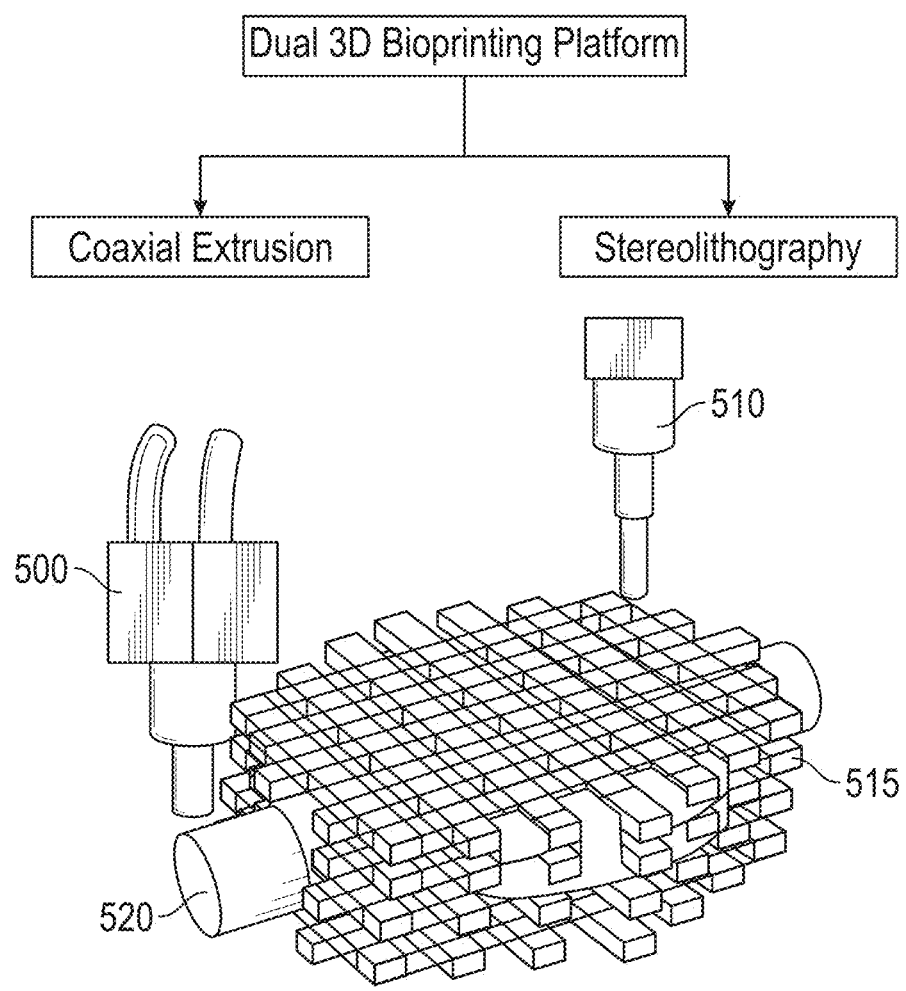
FIG. 5 is a diagram of a coaxial needle for producing vasculature embedded in a scaffold formed by stereolithographic 3D bioprinting.

Beyond the independent vasculature or blood vessels, bioprinting vasculature may be integrated into engineered tissue constructs for maintaining metabolic functions. FIG. 5 illustrates a coaxial needle 500 for producing 3D vasculature 520 within a scaffold 515 synthesized by stereolithography 3D bioprinting device 510. Human bone marrow-derived mesenchymal stem cell (hMSC)-laden GelMA hydrogel may be used as the universal tissue matrix model fabricated by stereolithography (SLA) bioprinting. The embedded vasculature may be designed to ensure uniform nutrient supplementation throughout the surrounding matrix.

Figure 6A:
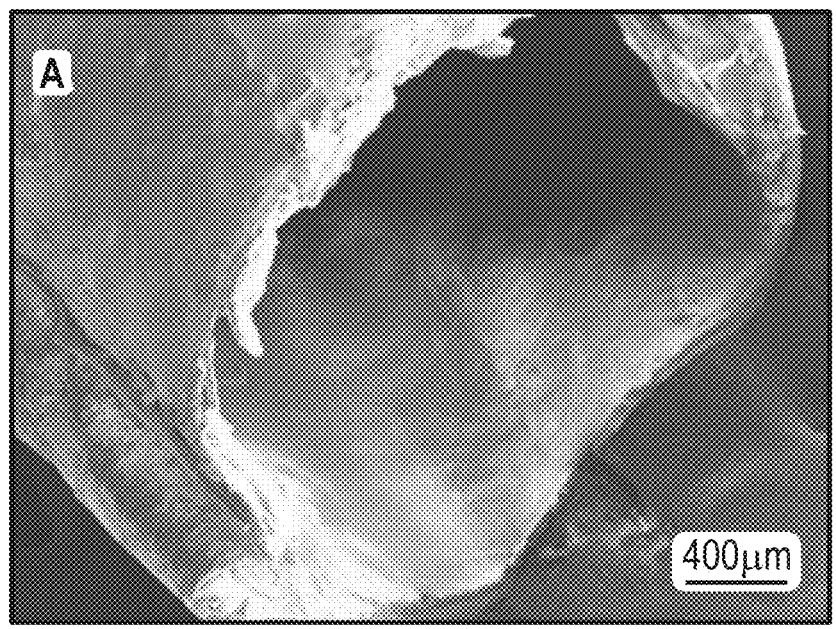
FIG. 6A is a scanning electron microscope (SEM) image of a 3D bioprinted blood vessel according to the disclosure herein.
Figure 6B:
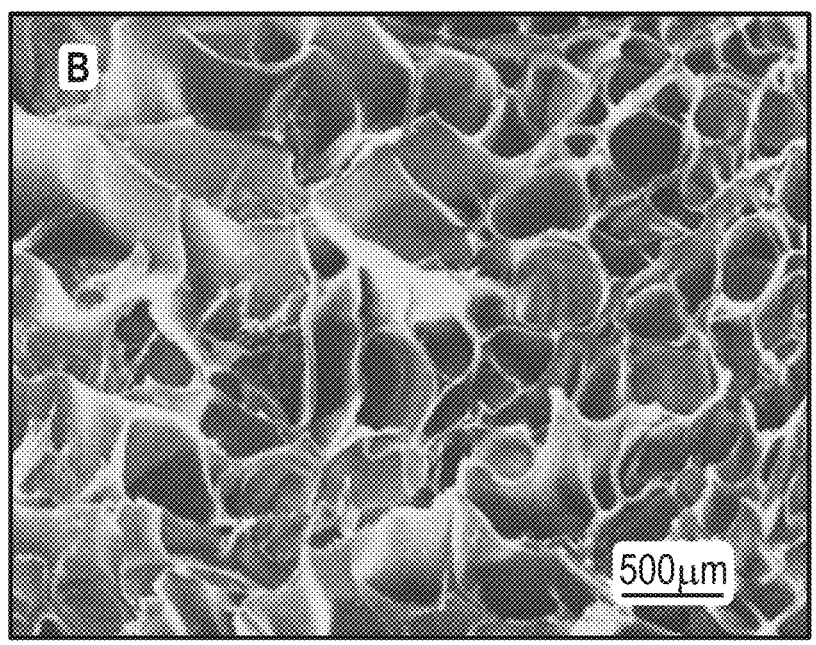
FIG. 6B is a locally amplified SEM image of the blood vessel hydrogel according to the disclosure herein.

Illustrated in FIG. 6A is a scanning electron microscope (SEM) image of a 3D bioprinted blood vessel according to the disclosure herein, magnified to 400 μm. FIG. 6B is a locally amplified SEM image of the blood vessel hydrogel, magnified to 50 μm.

Figure 7A:
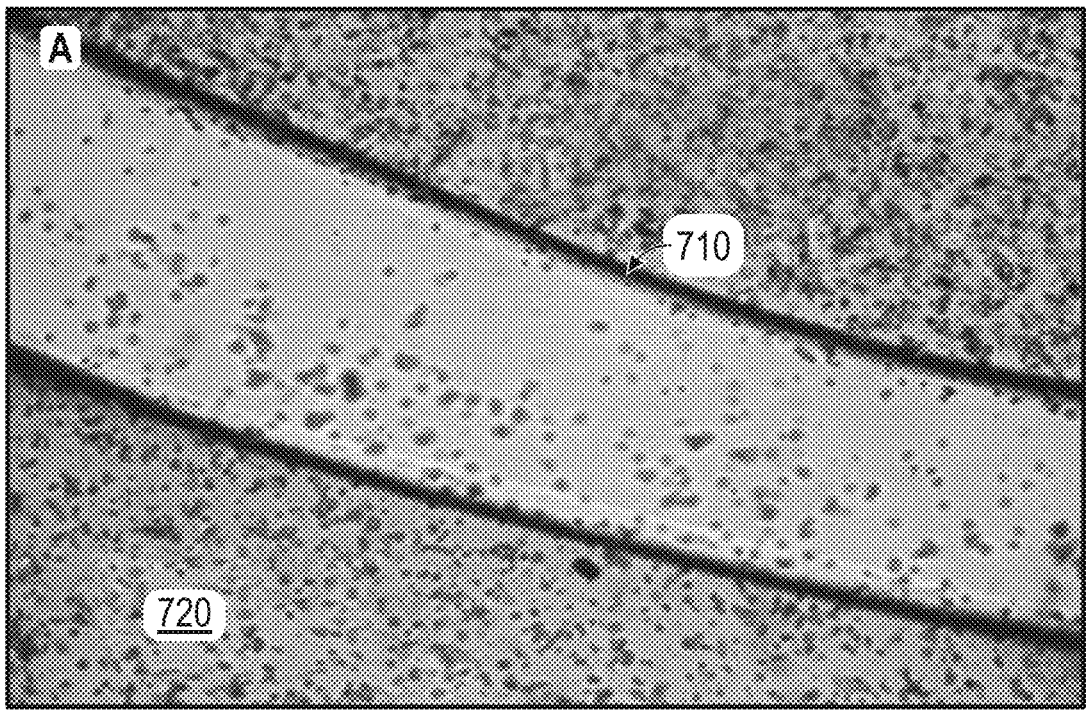
FIG. 7A is a light microscope image of 3D bioprinted blood vessels with a straight structure.
Figure 7B:
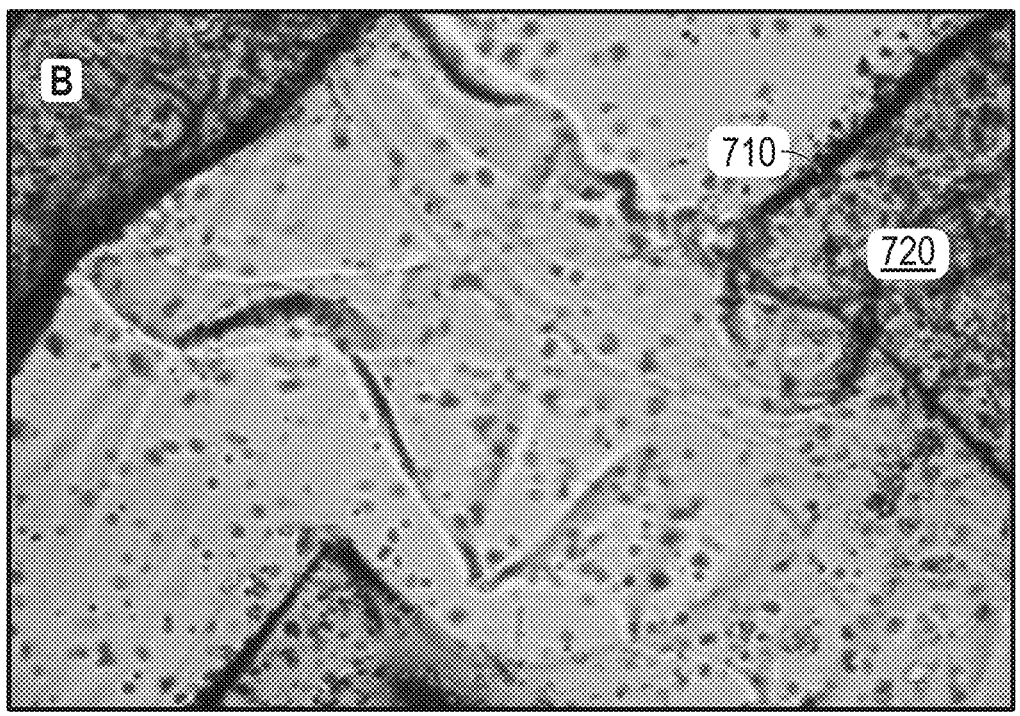
FIG. 7B a light microscope image of 3D bioprinted blood vessels with a branched structure.
Figure 7C:
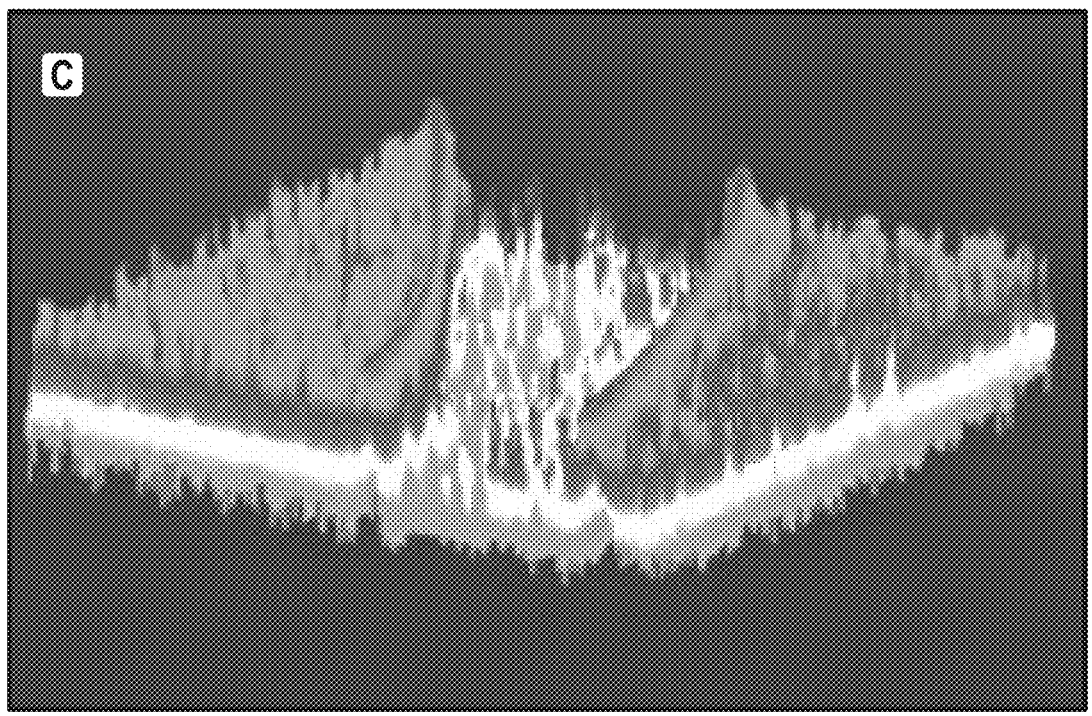
FIG. 7C is an image of finite-element model predictions of the 3D bioprinted blood vessels with a straight structure.
Figure 7D:
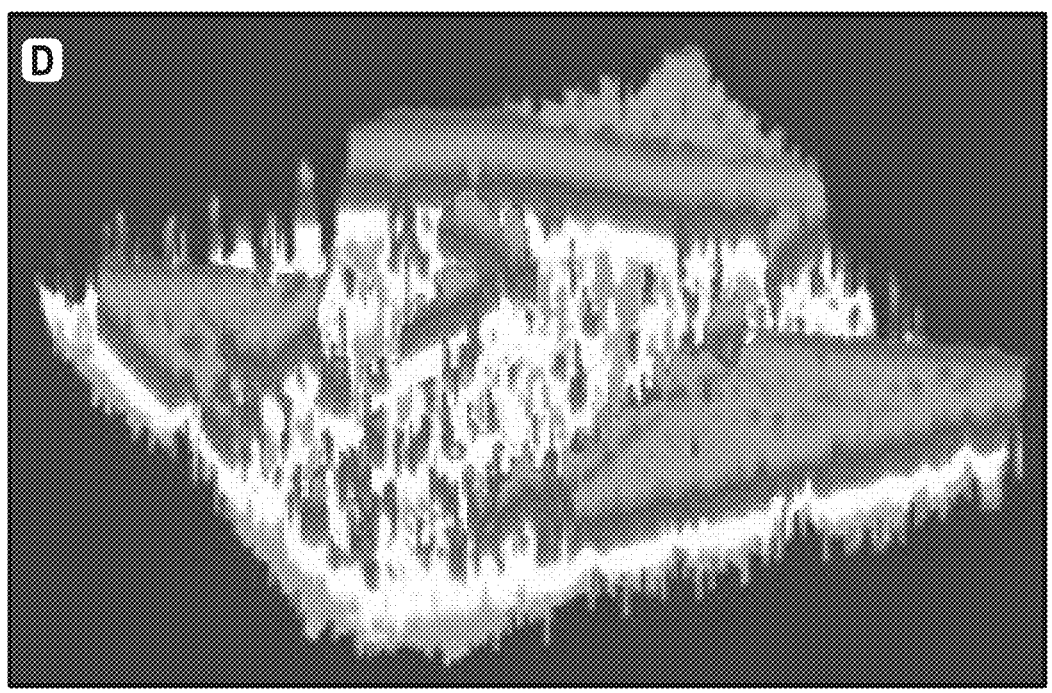
FIG. 7D is an image of finite-element model predictions of the 3D bioprinted blood vessels with a branched structure.

Illustrated in FIG. 7A is a light microscope image of 3D bioprinting blood vessels with a straight structure having endothelial cell layer 710 with surrounding smooth muscle cells 720. FIG. 7B shows a light microscope image of 3D bioprinting blood vessels with a branched structure also having endothelial cell layer 710 with surrounding smooth muscle cells 720. FIG. 7C illustrates finite-element model predictions of the 3D bioprinted blood vessels with straight structure and FIG. 7D illustrates finite-element model predictions of the 3D bioprinted blood vessels with a branched structure.

Figure 8A:
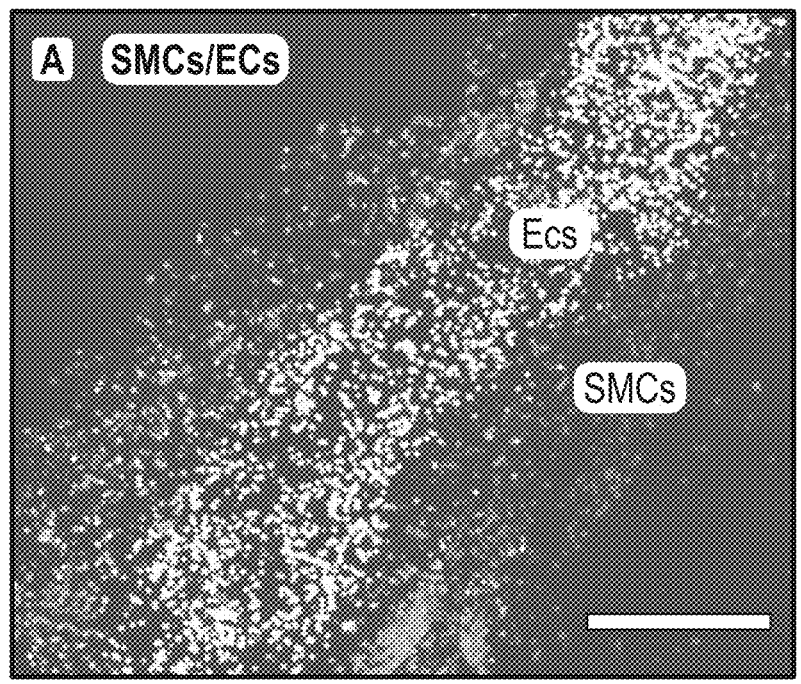
FIG. 8A is a confocal microscopy image of co-cultured smooth muscle cells surrounding the HUVECs in a straight blood vessel construct for 7 days.
Figure 8B:
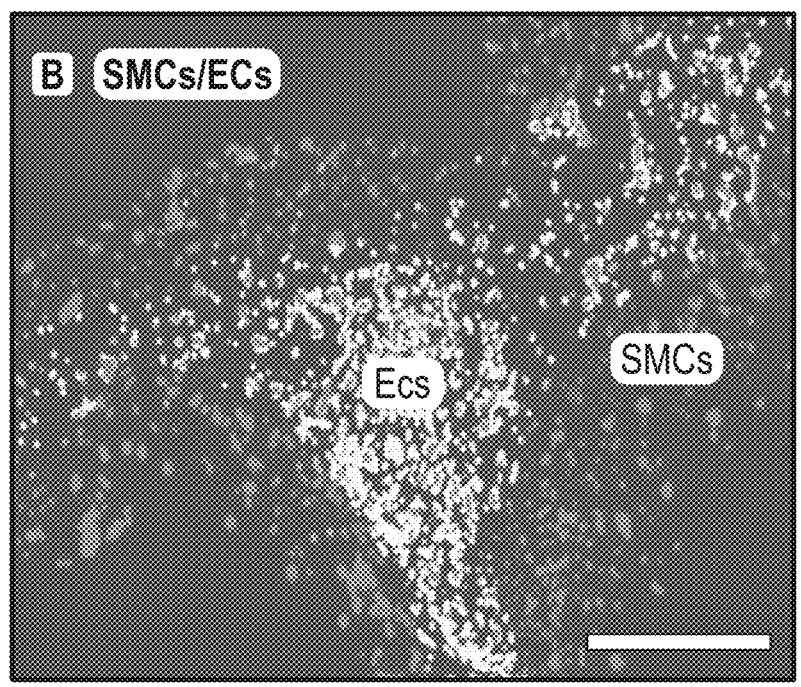
FIG. 8B is a confocal microscopy image of co-cultured smooth muscle cells surrounding the HUVECs in a branched blood vessel construct for 7 days.

FIG. 8A illustrates confocal microscopy images of co-cultured smooth muscle cells surrounding the HUVECs in a straight blood vessel construct for 7 days, and FIG. 8B illustrates confocal microscopy images of co-cultured smooth muscle cells surrounding the HUVECs in a branched blood vessel construct for 7 days. The scale shown for FIGS. 8A and 8B is 500 μm.

FIGS. 9A, 9B, 9C illustrate live-dead cell staining of smooth muscle cells encapsulated in blood vessel hydrogel after 1, 3 and 7 day cultures. The top row of FIGS. 9A, 9B, 9C show oxidation crosslinking [O] and the bottom row show UV enhanced crosslinking ([O]+UV). The cells were stained with calcein-AM/ethidium homodimer, and living cells were detected as green fluorescence and dead cells were detected as red fluorescence (displayed herein in black and white).

Figure 10A:
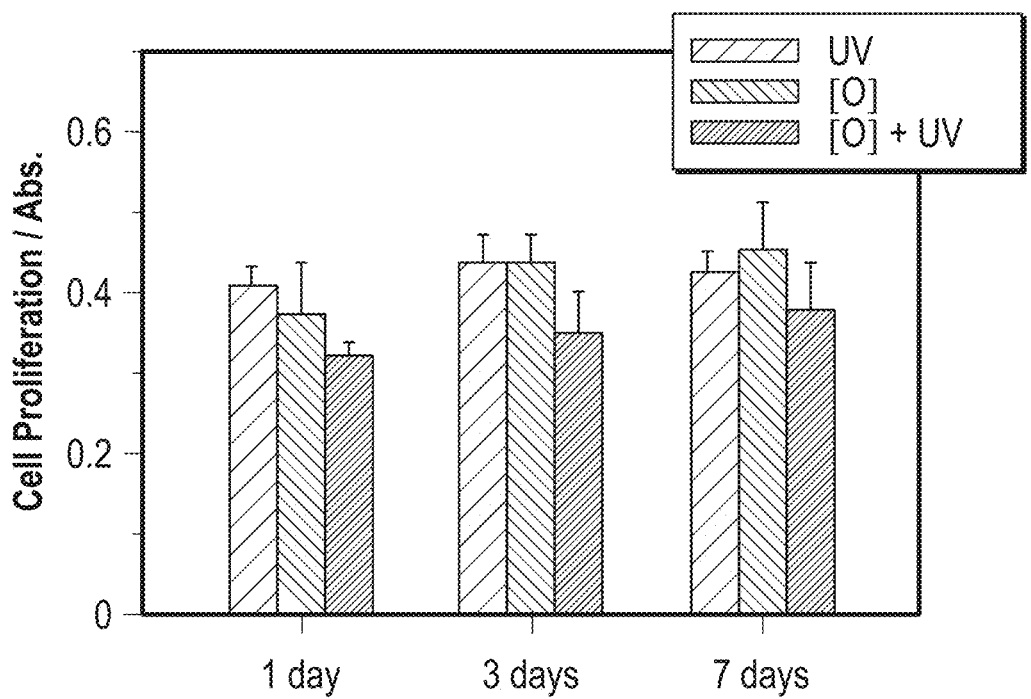
FIG. 10A is a graph illustrating cell proliferation quantified by cell count kit 8 (CCK-8) for smooth muscle cell encapsulated in 3D bioprinted hydrogels.
Figure 10B:
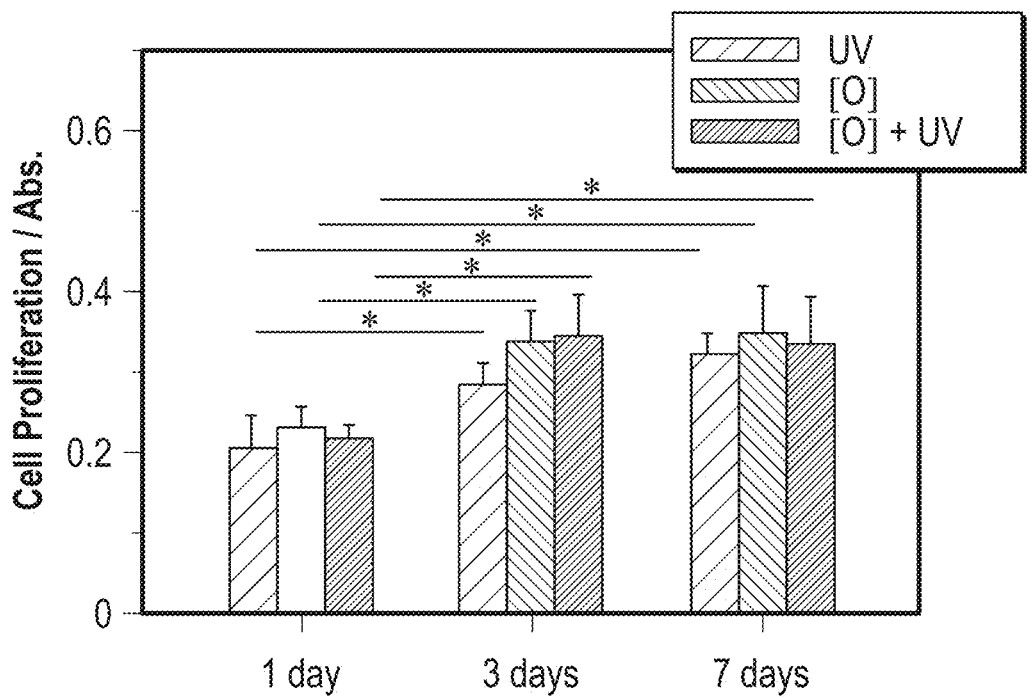
FIG. 10B is a graph illustrating cell proliferation quantified by CCK-8 for HUVECs seeded on the surface of hydrogels.

FIGS. 10A and 10B illustrate cell proliferation quantified by cell count kit 8 (CCK-8). As illustrated in FIG. 10A, smooth muscle cells were encapsulated in 3D bioprinted hydrogels and FIG. 10B illustrates HUVECs seeded on the surface of hydrogels. Three groups are UV crosslinking, oxidation crosslinking [O] and UV enhanced crosslinking ([O]+UV). The cell proliferation and absorbance was read at 450 nm via spectrometer (n–6, *p=>0.05). Data are expressed as a mean±standard deviation.

Figure 11:
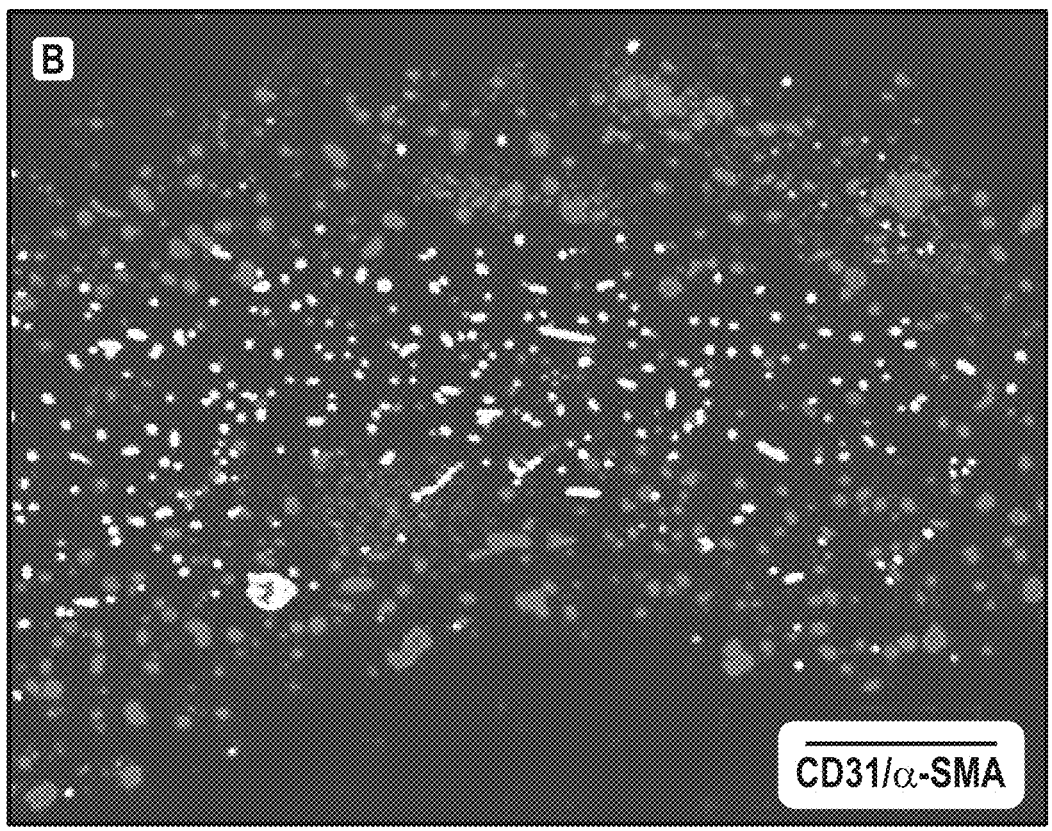
FIG. 11 is an image illustrating a dual layer blood vessel construct.

In order to mimic surrounding fluid presented in vivo, a bioreactor system utilized to study the functions of 3D bioprinted blood vessels. FIG. 11 illustrates a fluorescence image for alpha smooth muscle actin (α-SMA, represented by the outer darker dots) and CD31 antibody (represented by the inner lighter dots) showing that the dual layer blood vessel construct exhibited excellent myogenesis and angiogenesis (displayed herein in black and white).

With respect to FIGS. 12A, 12B, and 12C, locally amplified immunofluorescence staining of the 3D bioprinted blood vessels cultured in a bioreactor for 2 weeks. Smooth muscle cells were encapsulated in 3D printed hydrogel, while HUVECs were grown on the surface of the hydrogels. As shown the top row in FIGS. 11A, 11B, and 11C show endothelial cells and the bottom rows of FIGS. 11A, 11B, and 11C show smooth muscle cells with F-actin, blue nucleus (DAPI), and antibody for von Willebrand factor (vWF) and α-SMA as noted (displayed herein in black and white).

The embodiments shown and described above are only examples. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

We claim:

1. A method of forming a biomimetic blood vessel comprising:
flowing a bioink through an external needle passageway of a coaxial needle and out through a nozzle of the coaxial needle, the nozzle being at one end of the coaxial needle;
flowing a crosslinking solution through an internal needle passageway of the coaxial needle and out through the nozzle of the coaxial needle, the external needle passageway and internal needle passageway being separated by a barrier; and
contacting the crosslinking solution with the bioink as the crosslinking solution and the bioink exit the nozzle thereby forming a tubular blood vessel construct,
wherein the bioink comprises a gelatin methacrylate functionalized with a catechol.

2. The method of claim 1, wherein the bioink is cell-laden.

3. The method of claim 2, wherein the bioink is cell-laden with smooth muscle cells.

4. The method of claim 1, wherein the crosslinking solution comprises a crosslinking agent.

5. The method of claim 4, wherein the crosslinking agent is an oxidant.

6. The method of claim 5, wherein the oxidant is a periodate salt or a derivative thereof.

7. The method of claim 1, wherein the crosslinking solution comprises a removable fugitive ink.

8. The method of claim 7, wherein the fugitive ink comprises a block copolymer of ethylene oxide and propylene oxide.

9. The method of claim 1, wherein the crosslinking solution is cell-laden.

10. The method of claim 1, wherein the crosslinking solution is cell-laden with endothelial cells.

11. The method of claim 1, further comprising flowing a cell-laden fluid in a passageway between the external needle passageway and the internal needle passageway.

12. A system comprising:
a coaxial needle having an external needle passageway and an internal needle passageway separated by an internal barrier, and having a nozzle at an end thereof;
a bioink flowable through the external needle passageway; and
a crosslinking solution flowable through the internal needle passageway,
the crosslinking solution contacting the bioink as the crosslinking solution and bioink exit the nozzle thereby forming a tubular blood vessel construct,
wherein the bioink comprises a gelatin methacrylate functionalized with a crosslinkable group, and
the crosslinking solution comprises a crosslinking agent, wherein the crosslinking agent is a periodate salt or a derivative thereof.

13. The system of claim 12, wherein the crosslinking solution comprises a removable fugitive ink.

14. The system of claim 13, wherein the fugitive ink comprises a block copolymer of ethylene oxide and propylene oxide.

15. The system of claim 12, wherein
the bioink is cell-laden with smooth muscle cells, and
the crosslinking solution is cell-laden with endothelial cells,
wherein the tubular blood vessel construct comprises a bilayer of cells having an outer layer containing smooth muscle cells and an inner layer containing endothelial cells.

16. The system of claim 12, further comprising the tubular blood vessel construct being embedded in a scaffold.

17. A method of forming a biomimetic blood vessel comprising:
flowing a bioink through an external needle passageway of a coaxial needle and out through a nozzle of the coaxial needle, the nozzle being at one end of the coaxial needle;
flowing a crosslinking solution through an internal needle passageway of the coaxial needle and out through the nozzle of the coaxial needle, the external needle passageway and internal needle passageway being separated by a barrier;
flowing a cell-laden fluid in a passageway between the external needle passageway and the internal needle passageway; and
contacting the crosslinking solution with the bioink as the crosslinking solution and the bioink exit the nozzle thereby forming a tubular blood vessel construct.

18. The method of claim 17, wherein the crosslinking solution comprises an oxidant and a removable fugitive ink, wherein the oxidant is a periodate salt or a derivative thereof, and the removable fugitive ink comprises a block copolymer of ethylene oxide and propylene oxide.

19. The method of claim 17, wherein the bioink is cell-laden with smooth muscle cells.

20. The method of claim 17, wherein the crosslinking solution is cell-laden with endothelial cells.

21. A system comprising:
a coaxial needle having an external needle passageway and an internal needle passageway separated by an internal barrier, and having a nozzle at an end thereof;
a bioink flowable through the external needle passageway, wherein the bioink comprises a gelatin methacrylate functionalized with a catechol; and
a crosslinking solution flowable through the internal needle passageway, wherein the crosslinking solution comprises an oxidant or a derivative thereof,
the crosslinking solution contacting the bioink as the crosslinking solution and bioink exit the nozzle thereby forming a tubular blood vessel construct.

22. The system of claim 21, wherein the crosslinking solution comprises a removable fugitive ink, the fugitive ink comprising a block copolymer of ethylene oxide and propylene oxide.

23. The system of claim 22, wherein the crosslinking solution comprises endothelial cells.

* * * * *